United States Patent [19]
Cannata et al.

[11] Patent Number: 6,166,217
[45] Date of Patent: Dec. 26, 2000

[54] PROCESS FOR THE PRODUCTION OF ALKOXYCARBONYLDIPEPTIDES INTERMEDIATES IN THE SYNTHESIS OF THE LISINOPRIL

[75] Inventors: Vincenzo Cannata, Bologna; Valeriano Merli, Santa M. Maddalena; Stefano Saguatti, Bologna, all of Italy

[73] Assignee: AlliedSignal Inc., Morristown, N.J.

[21] Appl. No.: 09/335,811

[22] Filed: Jun. 18, 1999

Related U.S. Application Data

[62] Division of application No. 09/237,071, Jan. 25, 1999, Pat. No. 6,031,112.

[30] Foreign Application Priority Data

Feb. 9, 1998 [IT] Italy .................................. BO98A0063

[51] Int. Cl.[7] .................................................. C07D 263/44
[52] U.S. Cl. ................................................................ 548/227
[58] Field of Search ................................................ 548/227

[56] References Cited

FOREIGN PATENT DOCUMENTS 1 290 141   9/1972   United Kingdom .

OTHER PUBLICATIONS

T.J. Blacklock et al., "Large Scale N–Carboxyanhydride Preparation Of Ala–Pro And N $\epsilon$—(TFA) —LYS–PRO: Synthesis of Ace Inhibitors", Peptides: Structure and Function: Proceedings of the Nineth American Peptide Symposium 787–790, 1985.

Wu et al., Synthesis of . . . (Lisinopril), Journal of Pharmaceutical Sciences, 74(3), p. 352–353, Mar. 1985.

*Primary Examiner*—Joseph K. McKane
*Assistant Examiner*—Sonya N Wright
*Attorney, Agent, or Firm*—Colleen D. Szuch; Maria C. Walsh

[57] ABSTRACT

Process for the production of alkoxycarbonyldipeptides intermediates in the synthesis of the lisinopril which comprises protecting both amino functions of the L-lysine with an alkoxycarbonyl group, subsequently making the N-carboxyanhydride of the N6-[alkoxycarbonyl]-L-lysine by treatment with thionyl chloride and making the desired alkoxycarbonyldipeptide by reaction with L-proline in alkaline medium.

2 Claims, No Drawings

PROCESS FOR THE PRODUCTION OF ALKOXYCARBONYLDIPEPTIDES INTERMEDIATES IN THE SYNTHESIS OF THE LISINOPRIL

This application is a division of U.S. patent application Ser. No. 09/237,071 filed Jan. 25, 1999 now U.S. Pat. No. 6,031,112.

BACKGROUND OF THE INVENTION

The lisinopril is an important antihypertensive drug, described in U.S. Pat. No. 4374829, whose production can be carried out by passing through an intermediate alkoxycarbonyldipeptide. In the mentioned patent the intermediate N6-(tert-butoxycarbonyl)-L-lysyl-L-proline is used, intermediate whose synthesis is not described. Wu M. T. et al. have subsequently described the synthesis of this intermediate on J. Pharm. Sci., 74,(3), 352-4,(1985), synthesis which requires complex and expensive reagents.

It has now been found that alkoxycarbonyldipeptides equal or like to that described in the prior art can be obtained in a simple manner and with good yields by using easily accessible and cheap reagents.

DESCRIPTION OF THE INVENTION

A process for manufacturing alkoxycarbonyldipeptides useful in the synthesis of the lisinopril, important antihypertensive drug, is the object of the present invention. These alkoxycarbonyldipeptides present the general formula

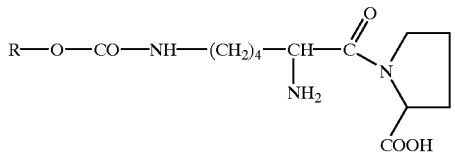

I wherein R represents a $C_1$-$C_6$ alkyl group, saturated or unsaturated, substituted or unsubstituted.

The R radical is a group selected from allyl, benzyl, ethyl, isopropyl, isobutyl, tertbutyl and trichloroethyl groups in a preferred aspect of the invention.

The process object of the present invention comprises:

a) protecting both amino functions of the L-lysine by treating the L-lysine in aqueous alkaline medium with an alkylchloroformate of general formula

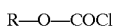

R—O—COCl   II in order to get a N2,N6-bis-(alkoxycarbonyl)-L-lysine of general formula

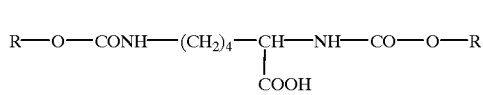

III b) reacting the product of general formula III in an inert solvent with thionyl chloride in presence of N,N-dimethylformamide in order to get the N-carboxyanhydride of the N6-(alkoxycarbonyl)-L-lysine of general formula

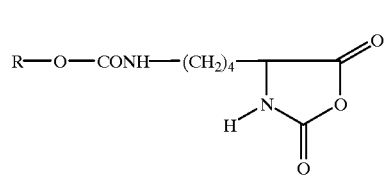

IV c) reacting the N-carboxyanhydride of general formula IV with L-proline in hydroacetonic alkaline medium in order to get the desired alkoxycarbonyl dipeptide of general formula I.

In a preferred aspect of the invention the reaction a) is carried out at a pH value between 10 and 12 at a temperature between 10° C. and 30° C. for a period of time between 2 and 6 hours; the reaction b) is carried out in an inert solvent selected from the halogenated hydrocarbons and the aromatic hydrocarbons at a temperature between 0°C. and 30° C. for a period of time between 2 and 6 hours; the reaction c) is carried out at a temperature between 0° C. and +10° C. for a period of time between 1 and 3 hours.

The hereunder described examples are a further illustration of the invention and do not have to be taken as a limitation thereof.

EXAMPLE 1

N2,N6-bis[(phenymethoxy)carbonyl]-L-lysine

In a four necked flask equipped with mechanic stirrer, thermometer, pH-meter and dripping funnel, 91.3 g (0.50 moles) of L-lysine hydrochloride are dissolved under stirring in 800 ml of water and then a 30% (w/v) aqueous solution of sodium hydroxide is added until the pH value is brought to 11.5. 185.3 Grams (1.05 moles) of 97% benzylchloroformate are added under stirring during one hour and half while keeping the temperature at 20° C.–25° C. and the pH value between 11.0 and 11.5 by addition of a 30% (w/v) aqueous solution of sodium hydroxide. The reaction is kept another hour and half under stirring while keeping the same values of pH and temperature, subsequently the pH value is brought between 7 and 8 by addition of a 30% (w/v) aqueous solution of hydrochloric acid, 500 ml of ethyl acetate are added and the pH value is brought between 1.0 and 1.5 always by addition of a 30% (w/v) aqueous solution of hydrochloric acid. The stirring is discontinued after 15 minutes and the layers are separated 20 minutes later. The aqueous layer is eliminated off while the organic layer is first washed with 150 ml of a 10% (w/v) aqueous solution of sodium chloride and then is evaporated to dryness obtaining 223.5 g of product in the form of an oily residue having a pureness equal to 87.2% with a yield equal to 94%.

EXAMPLE 2

N6-[(phenylmethoxy)carbonyl]-L-lysine, N-carboxyanhydride 44.38 Grams of N2,N6-bis[(phenylmethoxy)carbonyl]-L-lysine coming from example 1, 10.18 g of N,N-dimethylformamide and 266 ml of methylene chloride are mixed, at room temperature and under nitrogen atmosphere, in a four necked flask equipped with mechanic stirrer, thermometer and dripping funnel. The mixture is cooled to 0° C. and, under stirring, 16.54 g of thionyl chloride are added during 10 minutes; the reaction mixture is kept for one hour under these conditions and then at 10° C. for further two hours and subsequently it is evaporated under vacuum at a temperature lower than 40° C. obtaining 76 g of product in the form of a yellow-orange oil.

EXAMPLE 3

1-[N6-[(phenylmethoxy)carbonyl]-L-lysil]-L-proline 12.95 Grams of L-proline, 43.2 g of potassium carbonate, 7.42 g of 85% potassium hydroxide pearls and 387 ml of water are mixed at room temperature under stirring in a four necked flask equipped with mechanic stirrer, thermometer and dripping funnel. The obtained solution is then added with 295 ml of acetone, cooled to 2° C.-3° C. and then a solution cooled to 0° C. containing the 76 g of the product obtained in example 2 dissolved in 50 ml of acetone is quickly added. The reaction mixture is kept for one hour under stirring at 0° C. and then 200 ml of ethyl acetate are added.

The two layers are separated, the organic layer is eliminated off while the aqueous layer is washed with further 200 ml of ethyl acetate and then the pH is brought to a value between 8 and 9 by means of a 30% (w/v) aqueous solution of hydrochloric acid. The aqueous solution is concentrated to half volume under vacuum and then 200 ml of n-butanol are added and the pH of the mixture is brought to the 1.5 value by means of a 30% (w/v) aqueous solution of hydrochloric acid. The layers are separated and the aqueous layer is extracted again first with 200 ml and then with 100 ml of n-butanol. The three alcoholic extracts are collected, the pH is brought to about 5.0 with a 30% (w/v) aqueous solution of sodium hydroxide and the mixture is evaporated under vacuum obtaining an oily residue which is added with 100 ml of n- butanol and is evaporated again under vacuum. The residue is treated with other 100 ml of n-butanol under stirring and is filtered.

In this way 270 g of n-butanol solution containing 13.4% (w/v ) of product are obtained with a yield equal to 90%.

What is claimed is:

1. An N-carboxyanhydride of the general formula:

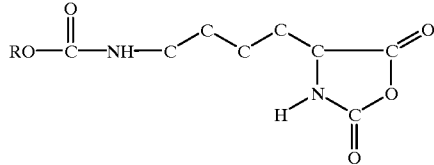

Wherein R represents a $C_1$–$C_6$ alkyl group, saturated or unsaturated, a benzyl group, or a trichloroethyl group.

2. The N-carboxyanhydride of claim 1, wherein R is a group selected from allyl, methyl, ethyl, n-propyl, isopropyl, n-butyl, isobutyl, tert-butyl, pentyl, hexyl and trichloroethyl.

* * * * *